US00PP16413P2

(12) United States Plant Patent
Zaiger et al.

(10) Patent No.: US PP16,413 P2
(45) Date of Patent: Apr. 4, 2006

(54) INTERSPECIFIC TREE

(50) Latin Name: [*(Prunus salicina×((Prunus salicina× Prunus armeniaca))×(Prunus salicina×(Prunus armeniaca))*]
Varietal Denomination: Flavor Royale

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 159 days.

(21) Appl. No.: 10/979,101

(22) Filed: Nov. 2, 2004

(51) Int. Cl.
*A01H 5/00* (2006.01)

(52) U.S. Cl. ..... Plt./180

(58) Field of Classification Search ..... Plt./180
See application file for complete search history.

*Primary Examiner*—Anne Marie Grunberg

(57) ABSTRACT

A new and distinct variety of interspecific tree [(plum× plumcot)×plumcot]. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combinations of desirable features:

1. Fruit with an attractive red flesh color.
2. Fruit with excellent flavor and eating quality.
3. Fruit having a good balance between sugar and acid with an average Brix of 17.7°.
4. The tree with a vigorous, upright growth habit.
5. Fruit with an attractive reddish maroon skin color.

1 Drawing Sheet

Botanical classification: [(*Prunus salicina*×((*Prunus salicina*×*Prunus armeniaca*))×(*Prunus salicina*×(*Prunus armeniaca*))].

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of interspecific tree was originated and asexually reproduced by us in our experimental orchard located near Modesto, Stanislaus County, Calif.

Prior Varieties

Among the existing varieties of plum, which are known to us, and mentioned herein, 'Red Beaut' Plum (U.S. Plant Pat. No. 2,539).

STATEMENT REGARDING FEDERALLY SPONSORED RESEARCH AND DEVELOPMENT

Not applicable.

Origin of the Variety

The new and distinct interspecific tree was originated by us from crosses of the following species, [(*Prunus salicina*× ((*Prunus salicina*×*Prunus armeniaca*))×(*Prunus salicina*× (*Prunus armeniaca*))]. The present new variety was selected from a first generation cross between the two proprietary parents with the field identification numbers 45GH74 and 42GA580. The maternal parent (45GH74) originated from an open pollinated seedling, the seedling of which was developed from the cross of a plum of unknown parentage and our proprietary plumcot (4G1180). The paternal parent (42GA580), which is a plumcot, originated from seed of an open pollinated 'Red Beaut' Plum (U.S. Plant Pat. No. 2,539). A large number of these first generation seedlings growing on there own root system were budded to trees of 'Nemaguard' Rootstock (non-patented) and under close and careful observation, one such budded tree exhibited desirable, early maturing fruit characteristics and was selected in 2001 for additional asexual propagation and commercialization.

Asexual Reproduction of the Variety

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

A new and distinct variety of interspecific tree [(plum× plumcot)×plumcot], which is of large size, vigorous, upright growth and a regular and productive bearer of large, red flesh fruit with excellent flavor and eating quality. The fruit is further characterized by its firm flesh, being relatively uniform in size throughout the tree and maturing in the early season. In comparison to 'Red Beaut' Plum (U.S. Plant Pat. No. 2,539), the fruit of the present variety has red flesh compared to yellow, is larger in size with heavier production and is approximately 6 days later in maturity.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of interspecific tree, 5 years of age, its flowers, foliage and fruit, as based on observations of a 5 year old specimen grown near Modesto, Calif., with color in accordance with Munsell Book of Color.

Tree:

*Size.*—Large, pruned to 3 to 3.5 meters in height and width, primarily for economical harvesting of fruit.

*Vigor.*—Vigorous, growth of 1.5 to 2 meters the first growing season, varies with fertility, type of soil and climatic conditions.

*Growth.*—Upright, similar to standard plum trees.

*Branching habit.*—Upright, crotch angle approximately 30°, increases with heavy production.

*Productivity.*—Heavy, sets from 1½ to several times more fruit than is desired, thinning and spacing of fruit necessary.

*Bearer.*—Regular, adequate fruit set 3 consecutive years. No alternate bearing observed.

*Fertility.*—Self sterile, pollenizer required.

*Density.*—Medium dense. Usually pruned to vase shape to allow more sunlight to center of tree to enhance fruit color and health of fruit spurs.

*Hardiness.*—Tree grown in USDA Hardiness Zone 9. Winter chilling requirement approximately 500 hours at or below 45° F.

Trunk:

*Size.*—Medium to large. Average circumference of 50.8 cm at 22.9 cm above ground on a 5 year old tree.

*Texture.*—Medium shaggy, becomes rougher with age.

*Color.*—Varies from 10YR 6/2 to 10YR 5/2.

Branches:

*Size.*—Medium. Average circumference 13.3 cm at 1.2 meters above ground. Crotch angle approximately 30°, increases with heavy crop load.

*Surface texture.*—New growth relatively smooth. Mature growth moderately rough, increases with age.

*Lenticels.*—Average number 16 in a 25.8 square cm section. Average length 4.0 mm. Average width 1.4 mm. Color varies from 7.5YR 6/8 to 7.5YR 6/10.

*Color.*—New growth varies from 2.5GY 6/6 to 2.5GY 5/6. Mature growth varies from 2.5YR 3/2 to 5YR 3/2, varies with age of growth.

Leaves:

*Size.*—Medium. Average length 99.1 mm. Average width 43.6 mm.

*Form.*—Oblanceolate.

*Apex.*—Acuminate.

*Base.*—Cuneate.

*Margin.*—Doubly serrate.

*Thickness.*—Medium.

*Surface texture.*—Upper surface relatively smooth, slight indentations over midrib and leaf veins, glabrous. Lower surface relatively smooth, except for small ridges created by midrib and pinnate venation, glabrous.

*Petiole.*—Size — medium. Average length 15.1 mm. Average width 1.5 mm. Grooved longitudinally. Surface glabrous. Color — lower surface 2.5GY 8/4, upper surface 5R 3/6.

*Glands.*—Reniform. Size — medium. Average length 1.1 mm. Average width 0.6 mm. Number — average 2, varies from 2 to 3. Located on lower portion of leaf blade and upper portion of petiole. Color varies from 5GY 5/6 to 5GY 5/5.

*Color.*—Upper surface varies from 5GY 4/4 to 5GY 4/6. Lower surface varies from 5GY 6/4 to 5GY 5/4. Midrib color varies from 5GY 9/4 to 5GY 8/4.

Flower buds:

*Size.*—Medium. Average length 11.2 mm. Average diameter 6.5 mm.

*Hardiness.*—Hardy in all stone fruit growing areas of California.

*Form.*—Conical, becoming elongated before opening.

*Pedicel.*—Size — medium. Average length 10.0 mm. Average width 0.6 mm. Color varies from 5GY 7/8 to 5GY 6/6.

*Color.*—N 9.5/.

*Number of buds per spur.*—Average number 4, varies from 2 to 8.

Flowers:

*Size.*—Medium. Average height 11.7 mm. Average diameter 23.5 mm.

*Petals.*—Number 5, alternately arranged to sepals. Size — medium. Average length 12.6 mm. Average width 8.8 mm. Form — obovate. Margin — sinuate. Both upper and lower surfaces glabrous. Color N 9.5/.

*Sepals.*—Number 5, alternatively arranged to petals. Shape — triangular. Margin — entire. Average length 4.2 mm. Average width 3.4 mm. Both upper and lower surfaces glabrous. Color of upper surface varies from 5GY 7/6 to 5GY 7/8. Lower surface varies from 5GY 8/6 to 5GY 7/6.

*Stamens.*—Average number per flower 31. Average filament length 8.9 mm. Filament color N 9.5/. Anther color varies from 5Y 9/6 to 7.5Y 9/6.

*Pollen.*—Present, but not strong. Self sterile, pollenizer required. Color varies from 5Y 8/8 to 5Y 8/10.

*Pistil.*—Normally one. Average length 11.3 mm. Position of stigma — average 1.9 mm above anthers. Color varies from 2.5GY 9/4 to 5GY 8/4. Surface — glabrous.

*Fragrance.*—Very slight.

*Blooming period.*—Date of First Bloom Feb. 14, 2003. Date of Petal Fall Feb. 24, 2003, varies slightly with climatic conditions.

*Color.*—N 9.5/.

*Number flowers per flower bud.*—Average number 2.

*Pedicel.*—Size — medium. Average length 12.0 mm. Average width 0.7 mm. Color varies from 2.5GY 6/8 to 5GY 6/6.

Fruit:

*Maturity when described.*—Firm ripe.

*Date of first picking.*—Jun. 4, 2003.

*Date of last picking.*—Jun. 12, 2003, varies slightly with climatic conditions.

*Size.*—Medium to large. Average diameter axially 60.1 mm. Average transversely in suture plane 68.5 mm.

Average weight 153.4 grams, varies slightly with fertility of the soil, amount of thinning and climatic conditions.

*Form.*—Globose.

*Suture.*—Nearly smooth, extends from base to apex.

*Ventral surface.*—Nearly smooth, slightly lipped.

*Apex.*—Varies from rounded to slight tip.

*Base.*—Retuse.

*Cavity.*—Rounded to slightly elongated in suture plane. Average depth 7.0 mm. Average diameter 13.7 mm.

Stem:

*Size.*—Large. Average length 14.4 mm. Average diameter 2.3 mm.

*Color.*—Varies from 5YR 4/6 to 7.5YR 4/6.

Flesh:

*Ripens.*—Relatively even, slightly early near skin surface.

*Firmness.*—Firm, comparable to 'Red Beaut' Plum (U.S. Plant Pat. No. 2,539).

*Fibers.*—Few, small, tender.

*Aroma.*—Slight.

*Amydgalin.*—Undetected.

*Eating quality.*—Excellent.

*Flavor.*—Good balance between acid and sugar.

*Juice.*—Moderate, enhances flavor.

*Brix.*—Average 17.7°, varies slightly with amount of fruit per tree and climatic conditions.

*Colors.*—Red mixed with yellow, varies from 5R 4/10 to 7.5R 3/10, mixed with 2.5Y 9/4 to 2.5Y 8/4. Pit cavity varies from 5R 4/10 to 7.5R 3/10.

Skin:

*Thickness.*—Medium.

*Surface.*—Smooth.

*Bloom.*—Moderate amount, complete coverage.

*Tendency to crack.*—Very slight.

*Color.*—Ground color varies from 10YR 8/4 to 2.5Y 8/6. Overspread with 2.5R 2/6 to 5R 2/6. Very small, randomly spaced areas of ground color exposed to skin surface giving a speckling pattern to skin.

*Tenacity.*—Tenacious to flesh.

*Astringency.*—Undetected.

Stone:

*Type.*—Clingstone.

*Size.*—Medium. Average length 21.2 mm. Average width 20.2 mm. Average thickness 9.8 mm.

*Form.*—Obovoid.

*Base.*—Usually flat, varies from flat to rounded.

*Apex.*—Slightly pointed. Average length 1.2 mm.

*Surface.*—Very lightly pitted throughout. One shallow groove on each side of suture extending from base to apex.

*Sides.*—Unequal, one side extending further outward from suture plane.

*Ridges.*—Very small and short extending from base toward apex on some stones.

*Tendency to split.*—None.

*Color.*—Varies from 5YR 5/6 to 5YR 4/8 when dry.

Kernal:

*Form.*—Ovate.

*Taste.*—Bitter.

*Viability.*—Poor viability, embryo partially developed.

*Size.*—Medium. Average length 14.4 mm. Average width 9.7 mm. Average depth 4.8 mm.

*Skin.*—Color varies from 5YR 8/8 to 5YR 4/8 when dry.

Use: Dessert. Market — local and long distance.

Keeping quality: Good, held firm 14 days in cold storage at 38° to 42° F. without internal breakdown of flesh or appreciable loss of flavor.

Shipping quality: Good, showed minimal skin scarring or flesh bruising of fruit in picking and packing trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

It is claimed:

1. A new and distinct variety of interspecific tree, substantially as illustrated and described, characterized by its large size, vigorous, upright growth and being a productive and regular bearer of medium to large, red flesh, clingstone fruit with excellent flavor and eating quality; in comparison to the early maturing fruit of 'Red Beaut' Plum (U.S. Plant Pat. No. 2,539), the fruit of the present variety is larger in size, has red flesh compared to yellow and is approximately 6 days later in maturity.

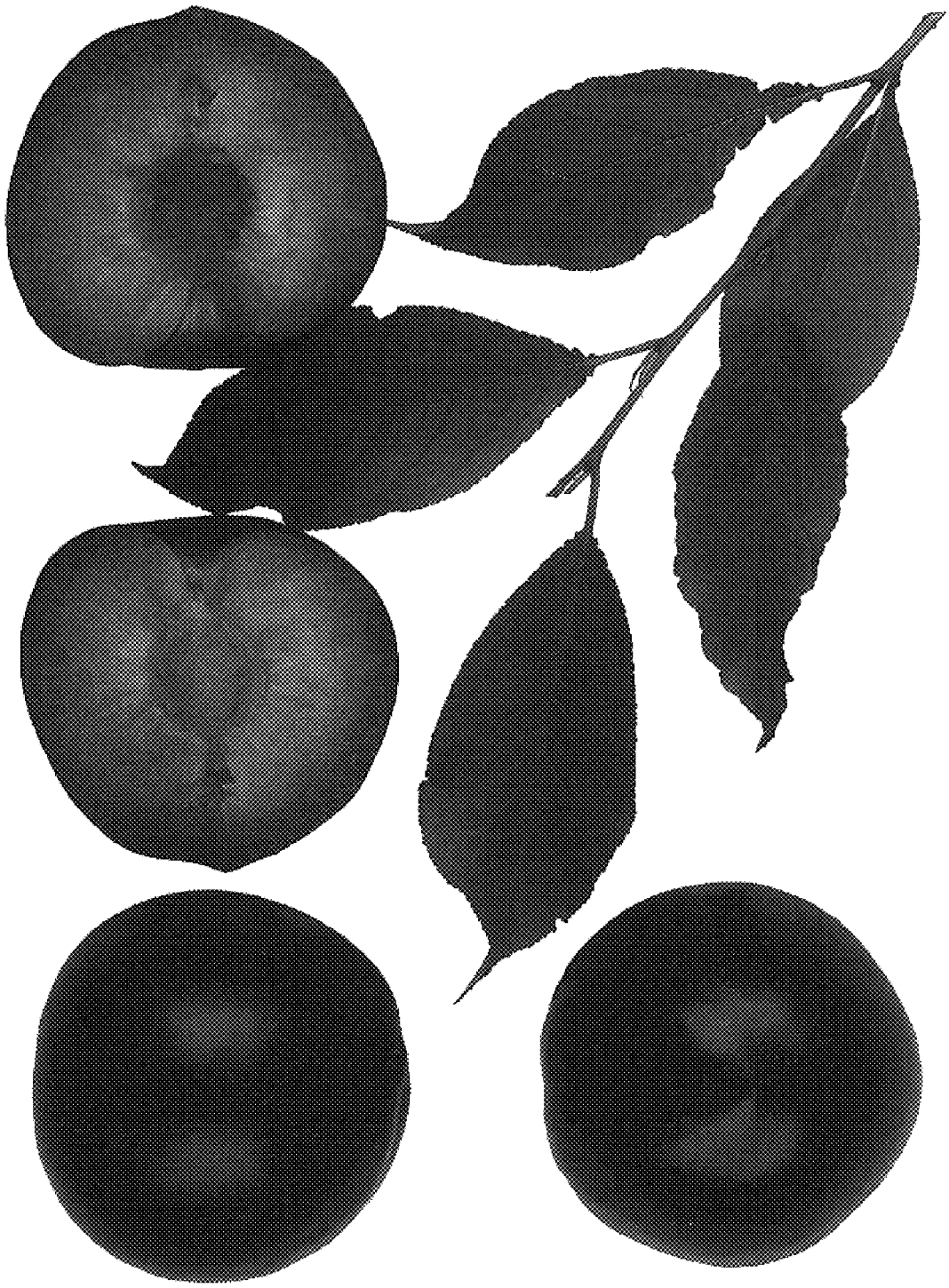

* * * * *